(12) United States Patent
Price et al.

(10) Patent No.: US 12,416,551 B2
(45) Date of Patent: Sep. 16, 2025

(54) APPARATUS FOR COLLECTION OF PARTICLES OF AN INHALABLE FORMULATION

(71) Applicant: NANOPHARM LIMITED, Newport (GB)

(72) Inventors: Robert Price, Monmouthshire (GB); Arron Danson, Herefordshire (GB); Gregor Strnisa, Radece (SI)

(73) Assignee: NANOPHARM LIMITED, Newport (GB)

( * ) Notice: Subject to any disclaimer, the term of this patent is extended or adjusted under 35 U.S.C. 154(b) by 715 days.

(21) Appl. No.: 17/776,411

(22) PCT Filed: Nov. 15, 2019

(86) PCT No.: PCT/EP2019/081543
§ 371 (c)(1),
(2) Date: May 12, 2022

(87) PCT Pub. No.: WO2021/093975
PCT Pub. Date: May 20, 2021

(65) Prior Publication Data
US 2022/0404240 A1    Dec. 22, 2022

(51) Int. Cl.
*G01N 1/22*    (2006.01)
*A61B 5/08*    (2006.01)
*A61B 5/087*    (2006.01)

(52) U.S. Cl.
CPC ........... *G01N 1/2205* (2013.01); *A61B 5/082* (2013.01); *A61B 5/087* (2013.01); *G01N 2001/2223* (2013.01)

(58) Field of Classification Search
CPC .. G01N 1/00; G01N 1/02; G01N 1/22; G01N 1/2205; G01N 2001/2223; A61B 5/082; A61B 5/087
See application file for complete search history.

(56) References Cited

U.S. PATENT DOCUMENTS 3,686,835 A  *  8/1972  Strange ................ G01N 1/2205
                                            73/863.25
3,949,594 A  *  4/1976  Treaftis ................ G01N 1/2205
                                            73/28.04
(Continued)

FOREIGN PATENT DOCUMENTS

CN      110243626 A        9/2019
DE       0636873 A1  *   2/1995  ........... G01N 1/2205
(Continued)

OTHER PUBLICATIONS

Machine Translation of EP-0636873-A1 (Year: 1995).*
(Continued)

*Primary Examiner* — Nguyen Q. Ha
(74) *Attorney, Agent, or Firm* — Sughrue Mion, PLLC (57) ABSTRACT

An apparatus for collecting aerosolized respirable particles of an inhalable medicinal formulation, having a dose collection section having an air-permeable filter extending across the pathway of the aerosolized respirable particles to retain particulate material on the filter. The dose collection section having an upper filter support member and a lower filter support member, the filter being circumferentially retained between the upper and lower support members to form a filter unit; a lower body receiving the filter unit, the lower body having recesses; and a quick-release system having hooks, movable between an open position and a closed position The hooks, in the open position, can enter the recesses around the filter unit, and in the closed position, can grab the filter unit, allowing removal of the filter unit without any human contact.

15 Claims, 5 Drawing Sheets

(56) References Cited

U.S. PATENT DOCUMENTS

| | | | |
|---|---|---|---|
| 5,404,762 A * | 4/1995 | Rodgers | B01D 46/10 |
| | | | 73/863.25 |
| 6,672,135 B2 * | 1/2004 | Adiletta | G01N 15/0272 |
| | | | 210/651 |
| 9,084,958 B2 * | 7/2015 | Wu | G01N 1/2205 |
| 10,520,439 B2 * | 12/2019 | Palmskog | G01N 33/497 |
| 2007/0044577 A1 | 3/2007 | Trakumas et al. | |
| 2016/0103043 A1 | 4/2016 | Skarping et al. | |
| 2018/0275022 A1 * | 9/2018 | Price | G01N 1/2208 |

FOREIGN PATENT DOCUMENTS

| | | |
|---|---|---|
| EP | 2 379 227 A1 | 10/2011 |
| WO | 2017/051180 A1 | 3/2017 |
| WO | 2018/149670 A1 | 8/2018 |

OTHER PUBLICATIONS

Written Opinion for PCT/EP2019/081543, dated Aug. 11, 2020.
International Search Report for PCT/EP2019/081543, dated Aug. 11, 2020.

* cited by examiner

APPARATUS FOR COLLECTION OF PARTICLES OF AN INHALABLE FORMULATION

CROSS REFERENCE TO RELATED APPLICATIONS

This Application is a National Stage of International Application No. PCT/EP2019/081543 filed Nov. 15, 2019.

FIELD OF INVENTION

The invention concerns an apparatus for collection of particles of an inhalable formulation.

BACKGROUND

Orally inhalable formulations are widely used for the administration of medications via the pulmonary route. Such medications are generally administered for treatment or prophylaxis of pulmonary conditions, the commonest of which include, for example, asthma and chronic obstructive pulmonary disorder. Also, drugs for systemic use may in appropriate circumstances be administered by inhalation.

The efficacy and systemic exposure (lung bioavailability) of an inhaled drug depends on the site of deposition and the physicochemical properties of the drug formulation. Drug particles that deposit in the peripheral non-ciliated regions of the respiratory tract must dissolve before metabolism or transport across the lung membrane can occur. Dissolution is therefore a prerequisite for cellular uptake and/or absorption via the lungs. Simulations suggest dissolution rate is the main driver for drug retention in the lung. At present, however, there is no pharmacopeial method which exists to determine the in vitro dissolution rate of aerosols generated by inhaled products.

Dissolution testing is an important tool in the determination of the bioavailability of many drugs. Standardized dissolution test methods are available for solid dosage forms such as tablets and capsules. Such methods are widely used in quality control and to determine correlations with in vivo release profiles. They are a particularly important tool where there is a necessity to demonstrate the bioequivalence of different formulations, for example in demonstrating the bioequivalence of generic drugs to an approved formulation. To date, however, there is no universally accepted method for estimating the dissolution behavior of inhaled active ingredient dosage forms. This presents an obstacle to the development of reliably bioequivalent formulations. The absence of a pharmacopeial method in particular presents an obstacle to reliably and reproducibly demonstrating bioequivalence of new inhalable generic drugs with pre-existing registered products, and thus renders the obtaining of authorization for inhalable drugs more difficult than in the case of most oral or injectable drug formulations. Studies have indicated good correlation between in vivo based measurements of total lung deposition and in vitro measurements of lung dose. Thus, there is a need to collect a representative lung dose for dissolution studies (e.g. ex-cast dose, impactor stage mass, dose below a defined impactor stage etc.). For all reported filter collection systems, there is a slower dissolution rate with increasing collected mass of a given formulation by varying the number of actuations. This effect is thought to be due to formation of in-situ agglomerates created on the filter upon dose collection, which in view of the smaller area/volume ratio reduces the exposure of the drug to the dissolution media during dissolution. Since the dissolution characteristics ought to be independent of the method of collection and the number of actuations, the absence of consistency in the dissolution rates is thought to be attributable to an artefact of the collection process. The significant variation observed in dissolution behavior limits sensitivity and creates challenges when comparing formulations with differing fine particle mass of the same product.

In any dissolution method, two key steps are the collection of the inhalable dose to be dissolved and the dissolution step of dissolving the collected dose. In order to provide a reliable prediction of the dose that will be dissolved in vivo, the sample used in the dissolution step should reflect the dose that, in practice, would be inhaled. In some known collection methods, the inhalable dose is collected on a filter in an inertial impactor.

A reliable method for estimating the dissolution behavior of inhaled products would have a number of applications. It could be applied in the context of quality control as a tool for evaluating material properties, and processing effects on active ingredient dissolution. It would be of general application in collection and dissolution studies of the aerosolized dose (e.g. ex-cast dose, impactor stage mass etc.). The most important potential application would be to provide an in vitro-in vivo correlation (IVIVC) technique. An IVIVC technique would have the potential to permit reliable evaluation of dissolution behavior of generic version of pulmonary drugs such as those evaluated on the basis of showing comparability with existing authorized products, thus reducing a current obstacle to the satisfactory evaluation of, for example, generic versions of inhalable drugs.

In conventional impactors, powders are separated using inertial effects, with the particles being separable according to their particle size by virtue of the variation of inertial behavior with particle size. Inertial separation techniques are advantageous in that they permit the physical separation according to particle size, thereby enabling the location of the deposition of the API as between particle size fractions to be determined. That can be important since the effectiveness and distribution of deposition of the API within the lung will be a function of their aerodynamic particle size. Impactors have a series of stages each made up of a plate, with multiple nozzles or jets. Air carrying the aerosolized powder is drawn into the impactor, and flows sequentially through the stages. The number of nozzles increase while the size and total nozzle area decrease with the stage number. As particles accelerate through the nozzles they either remain entrained in the air stream, which is deflected at the exit of the nozzle, or inertia causes them to be separated from the deflected flow, impacting on the collection surface. As direction of flow changes, aerosol particles continue to move in the original direction until they lose inertia. They then "relax" into the new flow direction (Relaxation time). Placing a collection surface normal to the original flow causes the particles which have insufficient relaxation time to impact. Small particles relax more quickly, thus do not impact. By controlling the number of nozzles or jets, their diameters (W) and the impaction stage separation (S) the effective cut-off aerodynamic diameter can be controlled at various flow rates. Thus, particles with a given level of inertia are collected, whilst the rest of the sample passes onto the next stage. Each stage of the impactor is therefore associated with a cut-off diameter, a figure defining the size of particles that are retained on the collection surface of that stage of the impactor device.

The main features of an impactor stage are a nozzle plate(s) through which the flow and entrained particles are delivered, an impaction plate and a stage wall. The design and engineering of the nozzle plate is most critical to the collection parameters, the number (N) of nozzles or jets and their diameter (W) being the major design parameters. Varying N and W allows the Reynolds number (Re) of the air flow to be controlled between set limits (generally 500<Re<3000). The relationship between the Reynolds number and the impactor geometry in an impactor type device is well understood by those skilled in the art (see for example Marple et al, Atmospheric Environment, 10, pages 891-896, 1976).

Except for stage 1 of the conventional impactors, in which a crude separation of large, non-respirable particles is accomplished, the nozzles of the known impactors are dimensioned and configured to generate a pressure difference which results in acceleration of the air flow as between a point immediately upstream of the nozzle and the region immediately downstream of the nozzle. This acceleration is important in generating the inertia required for the separation process at the subsequent deflection point. For example at stage 2 of a conventional impactor operating at an air flow of 60 L/min, the air flow through the nozzles may be typically accelerated to emerge as a multiplicity of air jets of air flow velocity of about 890 cm/s.

Document WO2017051180A1 discloses an apparatus that overcomes the drawbacks of the conventional impactors. Said apparatus has a dose collection section extending across the pathway and having an orifice, opposed to and upstream of the filter, which has an unimpeded area that is no less than 75% the area of the filter that is to be deposited on. A larger orifice provides an unimpeded pathway for delivery of the air flow onto the filter. As a consequence, the air flow in the filter unit (dose collection section) in the apparatus of the invention has a lower velocity, for example from 30 cm/s to 250 cm/s, preferably from 60 cm/s to 100 cm/s. It appears that the combination of lower flow velocity and greater uniformity of flow across the pathway enables more even deposition to take place, in contrast to the discrete high velocity air jets that are present on leaving the nozzles in a typical impactor stage. That enables greater reliability and reproducibility in determining the dissolution characteristics of the deposited material, which are less susceptible to variation in accordance with the amount of material deposited on the filter.

However, the apparatus disclosed in WO2017051180A1 also has drawbacks. In particular, said apparatus makes the removal of the drug loaded filters cumbersome, requiring a series of steps and a large degree of manual handling (e.g. removal of a number of "Allen key" screws to release the filter from the apparatus and the use of tweezers to remove filter from the apparatus and to transfer onto a secondary supporting assembly for dissolution testing etc.).

Non-Limiting Object of the Invention

The present invention has the goal to overcome the above drawbacks.

In particular, the present invention seeks to minimize the handling and to aid the ability to transfer the collected aerosol sample to a secondary apparatus for testing without direct human contact (e.g. dissolution testing, in vitro release testing, microscopy analysis etc.).

The present invention also aims to provide such an apparatus that is simple and cheap to manufacture and to assemble, an easy to use in a reliable manner.

The present invention thus provides an apparatus for collecting aerosolized respirable particles of an inhalable medicinal formulation, comprising a dose collection section having an air-permeable filter, said filter extending across the pathway of said aerosolized respirable particles so as to retain particulate material therein on said filter, said dose collection section comprising:

an upper filter support member and a lower filter support member, said filter being circumferentially retained between said upper and lower support members to form a filter unit, a lower body receiving said filter unit, said lower body having a top surface comprising recesses, a quick-release system comprising fixing means, such as hooks, movable between an open position and a closed position, wherein said fixing means, in said open position, can enter said recesses around said filter unit, and in said closed position, said fixing means can grab said filter unit, thus allowing removal of said filter unit from said lower body without any human contact on said filter unit.

Advantageously, said quick-release system further comprises a clamp base, an actuating rod, which actuation being triggered by a thumb-actuator, and a spring.

Advantageously, said lower filter support member comprises an outer ring connected to an inner flange projecting radially inwards from a lower surface of said outer ring, said inner flange having a peripheral inner edge defining a central opening, wherein said central opening has a central support structure connected to said peripheral inner edge by at least two radial ribs, thus defining multiple apertures.

Advantageously, said central support structure is hexagonal, with each apex of said hexagon being connected to the peripheral inner edge by a radial rib, thus defining seven apertures.

Advantageously, said upper filter support member comprises an upper ring and a lower ring, which extends axially downwards from said upper ring, said upper and lower rings having the same internal diameter, and said upper ring having an external diameter that is larger than the external diameter of said lower ring, wherein the external rim of said filter is retained between said inner flange of the lower filter support member and said lower ring of said upper filter support member.

Advantageously, said lower filter support member comprises at least one, preferably three, radial projections, extending radially outwards from the external periphery of said outer ring.

Advantageously, said top surface of said lower body comprises first recesses adapted to cooperate with said radial projections of the lower filter support member to provide rotational alignment of the filter unit on said lower body.

Advantageously, said apparatus further comprises:

an inlet for receiving an aerosolized dose of the medicinal formulation;

a suction source for generating a pneumatic flow through the apparatus;

a channel defining a pathway extending from said inlet to said suction source;

wherein the dose collection section is located in said pathway and comprises an inlet orifice, the filter being positioned opposed to said orifice, and the orifice being so dimensioned and configured that it has an unimpeded area that is no less than 75% of the area of said filter on which the dose will be collected;

wherein said suction source communicates with said pathway downstream of said filter unit;

wherein said filter unit has a filter and a filter support comprising one or more support members extending across the pathway on the surface of the filter opposed to the orifice for supporting a central region of the filter, the filter support defining two or more apertures and obstructing no more than 80% of the surface area of said opposed surface.

Advantageously, the orifice is so dimensioned and configured that it has an outlet area that is not less than 80%, preferably not less than 90%, of the area of said filter on which the dose will be collected.

Advantageously, said filter is selected from woven fabrics, nonwoven fabrics, meshes and air-permeable films.

Advantageously, the filter comprises a fabric formed from glass microfibers or from filaments of a polymeric material selected from polycarbonate, polyester, polyolefins, polyamides, polyvinylchlorides and polyetheretherketones.

Advantageously, the filter comprises a metal mesh, for example a stainless steel mesh.

Advantageously, said filter has a pore size of not more than 5 µm, preferably not more than 3 µm.

Advantageously, said filter has a pore size of at least 1 µm.

Advantageously, said filter has an air permeability which is such that the filter generates a reduction in flow rate of not more than 20%, preferably not more than 15%, more preferably not more than 10% relative to absence of a filter.

Definitions

"Inhalable medicinal formulation" is to be understood as referring to a formulation which is suitable for administration to a human or animal patient, preferably a human patient, by inhalation comprising one or more active ingredients that is effective in the treatment, prophylaxis or diagnosis of a disease or condition of a human or animal, especially a human, that is capable of pulmonary administration by inhalation. Inhalable formulations of the invention include, without limitation, powders for use in dry powder inhalers, formulations for use in metered dose inhalers, and solutions or suspensions for use in nebulizer devices.

"Powder formulations" as used herein refers to formulations which include particulate solids and, in the context of this specification, are preferably dry powder formulations for use in a dry powder inhaler device or formulations for use in metered dose inhalers.

"Active ingredient" in this specification is to be understood as including ingredients which are effective through any therapeutic route. For the avoidance of doubt active ingredients for the purpose of this application include therapeutically effective drugs that can be administered via the pulmonary route for local treatment, prophylaxis or diagnostic methods to be practiced on the lung, therapeutically effective drugs that can be administered via the pulmonary route for systemic treatment, prophylaxis or diagnostic methods to be practiced on one or more other parts of the body of the patient, and active ingredients that can be administered via the pulmonary route for local treatment, prophylaxis or diagnostic methods to be practiced on the lung by mechanical or physical routes, as in the case of lung surfactant. Active ingredients administered by the pulmonary route for local effect include, for example, drugs for use in the treatment of asthma, COPD, allergic rhinitis, cystic fibrosis, and tuberculosis. Systemic drugs administrable via the pulmonary route include for example insulin and small peptide therapeutics.

"Emitted dose" as used herein refers to the theoretical dose of an active ingredient that is expelled when an inhalation device is actuated. It may be equal to the theoretical total amount of the drug that is aerosolized, but may be less if the theoretical dose is not all successfully aerosolized.

"Particle" is used herein generally refers to solid particles unless the context implies otherwise.

"Respirable fraction" is used herein to refer to the fraction in % of particles that theoretically reaches the lungs of a typical patient on inhalation of a dose of a powder formulation. That fraction is generally understood by those in the art to be the sub fraction of the aerosolized particles of a powder formulation that have an aerodynamic diameter of less than 10 µm.

"Respirable dose" is used herein to refer to the amount of the emitted dose of a drug that theoretically reaches the lungs of a typical patient on inhalation of a dose of an inhalable medicinal formulation. The respirable dose may be estimated with a reasonable degree of accuracy as corresponding to the dose collected at or after Stage 2 in a conventional impactor (for example a Next Generation Impactor of MSP), also commonly referred to as the impactor stage mass ("ISM").

"Fine particle dose" as used in this specification refers to the dose of aerosolized drug particles with an aerodynamic diameter of less than 5µτι. To determine the Fine Particle Dose from an impactor requires either interpolation or regression based analysis of impactor data to determine the dose associated with an aerodynamic cut-off of 5µτι diameter particles.

"Aerodynamic diameter" is defined as the diameter of a sphere of density 1000 kg/m$^3$ with the same settling velocity as the particle of interest. Aerodynamic diameters may be ascertained by any of the methods customarily used by those in the art. Aerodynamic diameter values specified herein are as determined using a cascade impactor. Flow rates or velocities referred to herein are measurable using any suitable flow meter, for example a Copley DFM 2000 Flow Meter (Copley Scientific) which can be used for determining standard or volumetric flow rates.

"Unimpeded area" is used herein with reference to a pathway or an orifice as meaning that the pathway or orifice does not contain within the area any structure that would interrupt a pneumatic flow through that area of the pathway or orifice, and reference to a pathway or orifice with a given percentage unimpeded area is to be understood as being the percentage of the area of the orifice or area of cross section of pathway that is free from any structure that would, if provided within a region of the area of an orifice or pathway would interrupt a pneumatic flow through that region of the orifice or pathway.

BRIEF DESCRIPTION OF THE DRAWINGS

Certain embodiments of the invention will be described below with reference to the accompanying drawings, given as non-limiting examples, in which.

DETAILED DESCRIPTION OF CERTAIN EMBODIMENTS

The present invention is an improvement of the apparatus described in document WO2017051180A1, which is added herein as a reference. In that known apparatus, an aerosolized dose of medicinal formulation is generated at an inlet to the apparatus of the invention, and a suction device draws a pneumatic flow through the apparatus from a downstream access point. A dose collection section is provided in the pathway of the pneumatic flow through the apparatus. One particularly advantageous application of said apparatus is in relation to formulations for dry powder inhalers and metered dose inhalers. The respirable fraction of the aerosolized inhalable medicinal formulation is collectable in the dose collection section. That enables an accurate prediction to be made of the amount of the active ingredient of the formulation that is actually delivered into the lung of a typical patient.

In the apparatus of WO2017051180A1, the orifice is so dimensioned and configured that it has an unimpeded area that is no less than 75%, advantageously no less than 80%, for example no less than 90%, of the area of said filter on which the dose will be collected. In contrast, in a standard impactor device, a major part of the pathway is obstructed by a nozzle device having multiple nozzle jets, with the jets forming only a minority of the cross section of the nozzle device, with the result that the pneumatic flow passing through the jets is accelerated and leaves the jets in the form of multiple parallel jets at relatively high flow rates.

In the above apparatus, the pneumatic flow is delivered through an orifice of which only a minor proportion—no more than 25% of the area of the orifice—is impeded, which enables the pneumatic flow to be delivered to the filter along a pathway which is unimpeded or is no more than 25% impeded by structures that will interrupt the flow. Thus, in contrast to the known impactors, the above apparatus has a dose collection section in which the aerosol is delivered in a relatively uniform and relatively slow-moving flow, the entire flow being directed onto a collection filter. This flow pattern is in contrast to the nozzles (also referred to as "jets") that accelerate the pneumatic flow in known impactors for the purpose of achieving inertial separation.

In some embodiments there may be present in the pathway upstream of the orifice of the dose collection section a first removal device for removal of particles of particle size of 10 μm or greater and optionally one or more further removal devices for removal of one or more additional particle size fractions. A removal device for removal of particles of a given particle size may, for example, be a stage or stages of an impactor, especially an inertial separating stage arranged to separate particles in excess of a certain aerodynamic diameter. Where more than one further removal devices are present, those may include two or more impactor stages arranged in series arranged for inertial separation of successively smaller size particle fractions. Thus, for avoidance of doubt, the apparatus of WO2017051180A1 may additionally include such multiple nozzle structures in parts of the pathway upstream of the collection device, for example in one or more inertial removal devices optionally present for removal of one or more particle size fractions from the aerosolized formulation prior to reaching the dose collection section. The removal of particle size fractions that may normally be considered to be within the respirable fraction may be useful, for example, when attempting to replicate the respirable fraction of patients with respiratory function that is lower than that of the average adult patient, for example in the case of children, neonates, or adults with impaired respiratory function. Suitable as removal device is in particular an inertial removal device. An inertial removal device used in the invention may optionally comprise a deflection region in said pathway, whereby particles having less than a predetermined aerodynamic diameter are deflected with the pneumatic flow in said deflection region and particles having an aerodynamic diameter greater than said predetermined aerodynamic diameter are flung out of the pathway by inertial effects. For example, there are commercially available devices known as "anatomical throats" which are suitable for removing larger particles. Such devices have been demonstrated to filter an inhalation dose such that the does passing the throat correlates well with the dose found to have entered the lung in in vivo lung deposition studies. In some embodiments, there is provided in said pathway between said removal device and said dose collection unit one or more inertial separation units for elimination of one or more further particle size fractions from the pneumatic flow before it reaches said dose collection unit.

The dose collection section comprises a filter unit located downstream of the orifice, wherein the filter unit comprises said filter.

The necessary flow characteristics to achieve uniform deposition on the filter are achievable by appropriate selection of the orifice area. Since in practice the orifice area will generally be circular, the discussion hereafter is given with reference to a circular orifice. It is to be understood, however, that the orifice is not necessarily circular in configuration and may be of any suitable configuration, for example, oval, square, or rectangular, the configuration of the filter preferably being selected to be similar or the same as that of the orifice. In practice, the orifice diameter is selected to be greater than the diameters of nozzles conventionally used in nozzle plates of impactor devices. For example, the diameter of the orifice may advantageously be at least 10 mm in diameter, advantageously at least 15 mm in diameter, especially at least 20 mm in diameter. In practice, it will generally be preferred that the diameter of the orifice is not more than 50 mm, for example not more than 45 mm, especially not more than 40 mm.

In practice, it has been found expedient for the orifice to be provided by a tapered member, the taper being such that there is defined at the outlet an orifice diameter value as specified above. The use of a tapered member has been found to reduce turbulence effects.

The unimpeded area of the orifice through which the airflow is delivered onto the filter is not less than 75% of the area of the filter on which deposition takes place. The diameter of the filter is advantageously at least 10 mm, preferably at least 15 mm, for example at least 20 mm. Advantageously, the filter has a diameter not exceeding about 60 mm, more advantageously not exceeding about 50 mm, for example not exceeding about 45 mm. It will be appreciated that it will be possible in principle to use a filter of larger dimensions. In that case, it is to be understood that, for the purpose of determining the relative sizes of the orifice and the filter, the area of the filter for that purpose is that area in which at least 90% by weight of the collected material is deposited.

The Reynolds number is the ratio of the inertial forces to viscous forces and can predict the type of flow which will occur in a particular situation. In the design of the nozzles in an impactor, varying the number of nozzles and the width of the jets enables the air flow to be controlled between set limits to maintain laminar flow. Typically, the number of jets is chosen to control the Reynolds number. To maintain laminar flow over a range of flow rates, the limit of Re (Reynolds number) should ideally be between 500 and 3000.

In practice, it has been found that a round orifice of diameter 2 to 5 cm, preferably 2.5 to 5 cm, more preferably 3 to 5 cm, for example 3 to 4.5 cm is suitable. Such dimensions have in particular been found to be advantageous where, in use, flow rates of 10 to 100 L/min, for example, 15 to 100 L/min, especially 15 to 70 L/min are used, for example flow rates of 30 L/min or 60 L/min.

Advantageously the pathway comprises a tapered portion leading to the orifice.

In one embodiment the nozzle diameter has an internal diameter of 4.5 cm at the top of the nozzle section and reduces to 3.9 cm at the opening. The reducing diameter is advantageous in that it reduces the presence of sharp angles which may induce turbulence. It is preferred that the filter, or at least that part of the filter on which deposition occurs, is of substantially planar configuration.

The apparatus of WO2017051180A1 includes a dose collection section, which as mentioned above includes a filter F. The filter is arranged orthogonally with respect to the direction of flow of the pneumatic flow downstream of the orifice. As already mentioned, it is desired that, at the point of impact with the filter, the conditions are of relatively uniform and low-velocity pneumatic flow. In practice, that may be achievable by appropriate selection of the dimensions of the orifice and appropriate selection of the spacing between the orifice and the filter. It is preferred that the orifice has a diameter of not less than 14 mm. The distance between the orifice and the filter is advantageously not more than three times the diameter of the orifice, for example up to twice the diameter of the orifice. Where the distance between the orifice and the filter is large, interference as a result of deposit of material on the wall may adversely affect collection efficiency, and in practice it may be desirable for the separation distance to be considerably shorter than three times the diameter of the orifice. By way of illustration in some embodiments the distance between the orifice and the filter may be up to 10 cm, for example from 1 to 10 cm. It is preferred that the portion of the pathway extending from the orifice to the filter is straight and is uninterrupted or substantially uninterrupted by any structures that would materially interfere with the uniformity of the flow.

Advantageously, the filter F obstructs at least a portion of the pathway at a point downstream of the orifice. In some embodiments, the filter obstructs substantially the entire pathway.

Advantageously, the filter support comprises elongate support members extending across the pathway on the surface of the filter opposed to the orifice for supporting a central region of the filter, the filter support defining from two to ten apertures.

It has been found that providing a substantial area of support structure under the filter influences undesirably the pattern of deposition of solids on the filter. It is believed that, whilst the passing of the air through the filter inevitably disrupts to some extent the uniformity of flow, the provision of support structures under the filter significantly influences the flow in such a way that it is disrupted upstream of the filter so as to form preferential islands of agglomerated deposition at points where the carrier air is free to pass through the filter. For that reason, it is preferred that as much as possible of the underside of the filter, for example at least 75%, remains completely unobstructed thereby avoiding any undue effect on the uniformity of the flow as it passes through the filter. It is a particular advantage of the apparatus of the invention that the aerosolized particles are captured across the entire surface of the filter rather than being deposited in well-defined locations in relation to the position of delivery jets (as in certain known apparatus) or in relation to support structures obscuring the pathway under the filter.

The filter can be any filter that is appropriate for retaining particles in the range of up to 5 μm, for example in the range of from 0.45 μm to 5 μm. For example, filters with a pore size of up to 3 μm can be used.

Advantageously, the filter has an air permeability which is such that the filter generates a reduction in flow rate of not more than 20%, preferably not more than 15%, more preferably not more than 10% as compared with the flow rate in absence of a filter. Such filters may, but do not necessarily, have a pore size of at least 1 μm.

The filter may, for example, be selected from woven fabrics, nonwoven fabrics, meshes and air-permeable films. In some embodiments, the filter comprises a fabric formed from glass microfibers or from filaments of a polymeric material selected from polycarbonates, polyesters, polyolefins, polyamides (for example nylons), acrylics, acrylic copolymers, polyvinylchlorides and polyetheretherketones. Suitable polyolefins include, for example, polyethylene, polypropylene and ethylene and propylene copolymers with one or more other monomers. The filter can also comprise synthetic cellulose based materials, as for example cellulose acetate, cellulose nitrate and mixed cellulose ester synthetic membranes.

Suitable glass microfibers include, for example, borosilicate glass, such as the glass fiber filters commercially available from Pall Corporation, USA as Type A/E, with a nominal pore size of 1 μm. Illustrative of suitable polymer filters include acrylic co-polymer filters with a pore size 3 μm or less, for example those with pore sizes of 0.2, 0.45, 0.8, 1.2 and 3 μm. Polymer filters of polyamide or of polyvinylchloride with a nominal pore size of 3 μm or less are also widely commercially available. This is also true for cellulose based membranes.

In other embodiments, the filter comprises a metal mesh, for example, of stainless steel, which advantageously has a pore size of less than 3 μm. Other suitable materials include, for example, polymer films provided that they have a suitable level of air permeability.

Advantageously, collected particles are subjected to a dissolution test. Dissolution tests are widely practiced in the art and the selection of suitable dissolution media and methods for particles collected from a given drug formulation are a routine matter for those skilled in the art. One such test, which may be expediently used, is the paddle over disk dissolution test (US Pharmocopeial Convention 2011, 711, Dissolution, Paddle over Disk Apparatus). Commonly used dissolution media include e.g. phosphate buffered saline (PBS) solution either with or without the addition of a surfactant (e.g. Tween 20, Tween 80, SDS etc.). The solution can be chemically analyzed, for example by HPLC, to determine the mass collected.

One advantageous embodiment of the dose collection section in the apparatus of the invention is shown in FIGS. 1 to 13.

Figure 1:
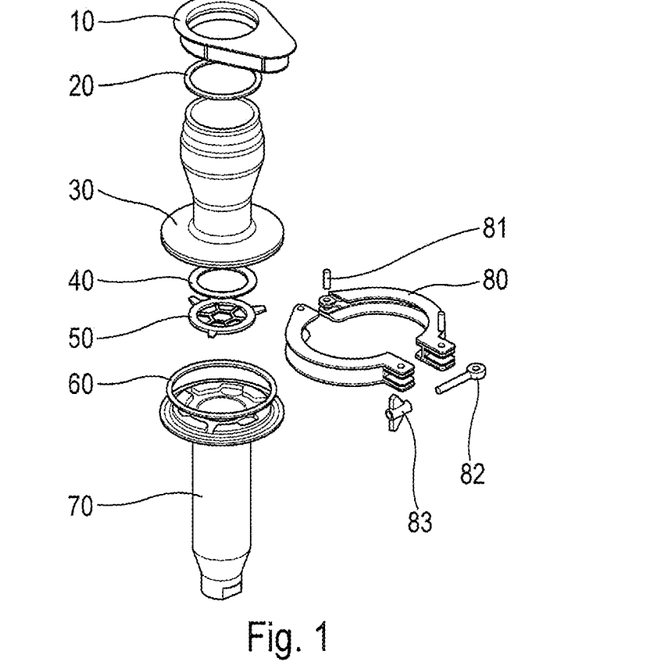
FIG. 1 is a schematic exploded perspective view of a dose collection device according to an advantageous embodiment of the present invention.

The dose collection device of FIG. 1 comprises, taken from the top to the bottom of FIG. 1, an upper adapter element 10, a first O-ring 20, an upper body 30, an upper filter support member 40, a lower filter support member 50, a second O-ring 60, a lower body 70 and a clamping device 80, used to clamp upper and lower bodies together, thus compressing the second O-ring 60.

Upper body 30 comprises a funnel 31 that defines an inlet orifice 32. The funnel 31 is tapered to reduce the occurrence of sharp edges, which may induce turbulence, and is arranged to deliver the fluid flow into an unimpeded vertical pathway extending downwardly from orifice 32 towards the filter collection device.

The filter F is supported by a filter unit comprising the upper filter support member 40 and the lower filter support member 50. The filter F thus is circumferentially retained between said upper and lower support members.

The area of orifice 32 is similar to, but slightly less than, the exposed area of filter F on which deposit occurs.

Figure 2:
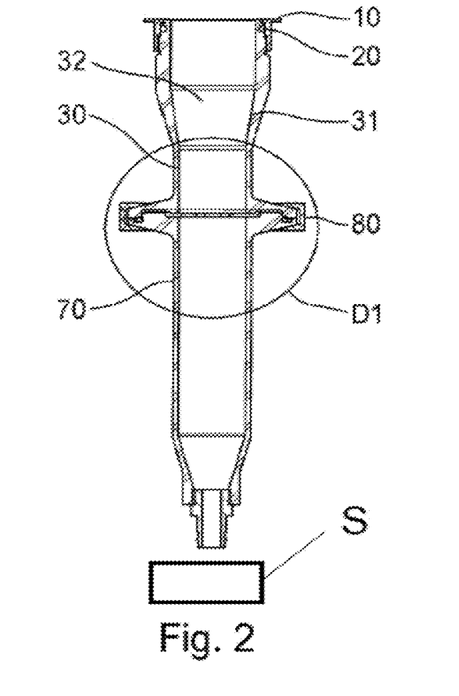
FIG. 2 is a sectional view through the device of FIG. 1.
Figure 3:
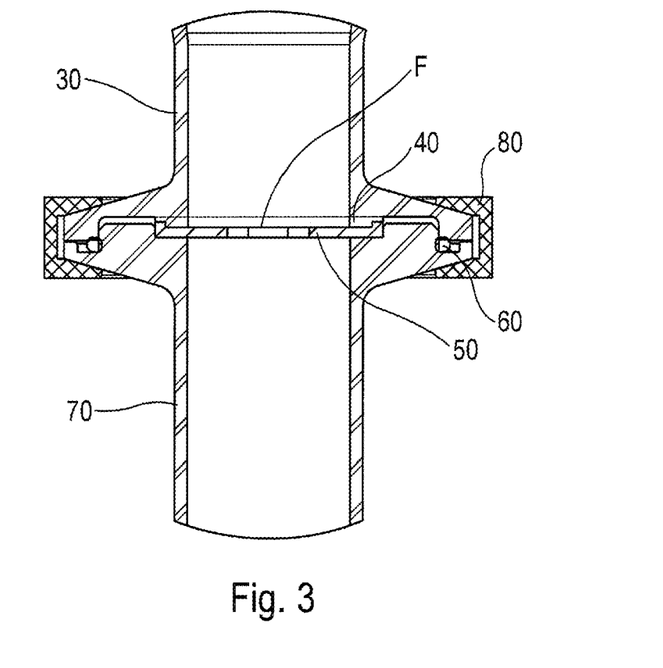
FIG. 3 is an enlarged view of detail D1 of FIG. 2.

A suction source, schematically shown in FIG. 2, is in pneumatic communication with the filter on the side remote from the orifice and serves to draw air through the pathway including the orifice 32, and filter F in the downward direction in FIGS. 2 and 3.

A flow controller (not shown) is associated with the suction source for maintaining suitable flow conditions.

The lower filter support member 50 is configured to have minimal contact with the filter F. A suitable filter unit is shown in FIGS. 6 to 9.

The lower filter support member 50 comprises an outer ring 57 connected to an inner flange 56 projecting radially inwards from the lower surface of said outer ring 57, said inner flange 56 has a peripheral inner edge 52 defining a central opening.

The lower filter support member 50 comprises at least one, preferably three, radial projections 55, extending radially outwards from the external periphery of said outer ring 57.

Figure 4:
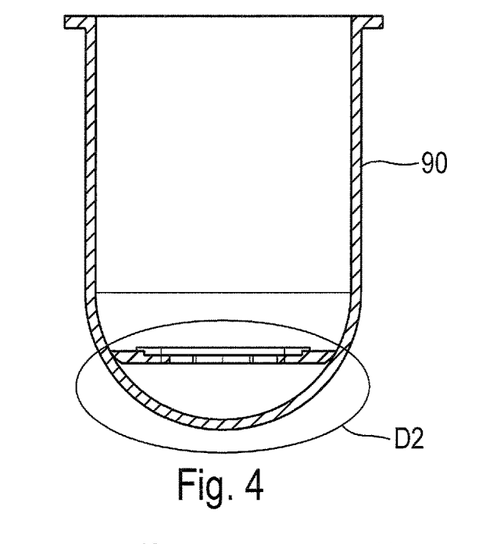
FIG. 4 is a sectional view of a dissolution vessel receiving the filter unit of FIG. 3.
Figure 5:
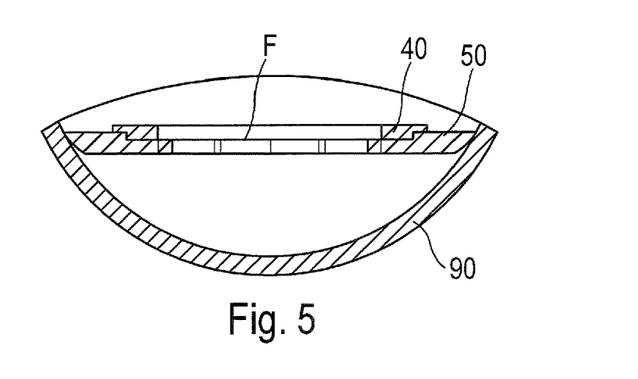
FIG. 5 is an enlarged view of detail D2 of FIG. 4.
Figure 6:
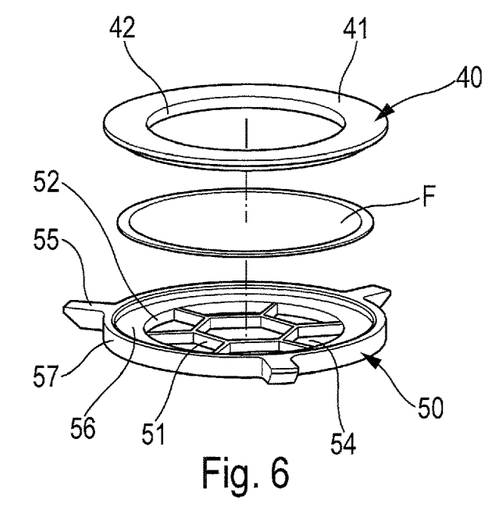
FIG. 6 shows an exploded perspective view of the filter unit of FIG. 5.

One function of said radial projections 55 is to correctly align the filter unit at the right depth within a dissolution vessel 90 for dissolution studies, as seen on FIGS. 4 and 5. The dissolution vessel 90 is preferably a mini-Erweka dissolution apparatus. Advantageously, the radial projections 55 are tapered on their lower surface, which improves the positioning of the filter unit in the rounded bottom part of the dissolution vessel 90, allowing quick, accurate and reproducible positioning of the assembly within the dissolution vessel 90. It also ensures that the filter unit remains orthogonally aligned to the paddle stirrer and at the correct distance between the filter surface and the paddle during dissolution measurements.

Another function of said radial projections 55 is to provide rotational alignment with the lower body 70. This ensures that semi-automated or automate equipment can correctly register the filter unit position. The outer ring 57 ensures co-axial alignment with the upper and lower bodies 30, 70 and the inner flange 56 enables sufficient contact surface for sealing of the filter F.

Figure 7:
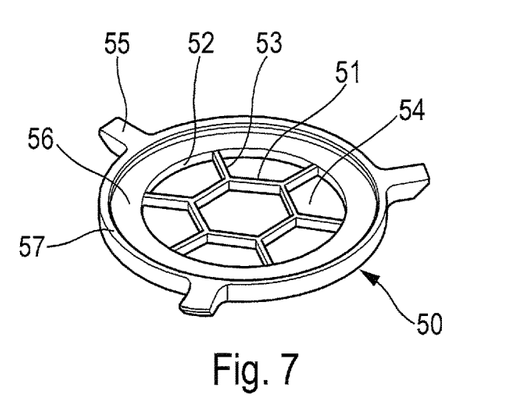
FIG. 7 shows a perspective view of the lower filter support member.
Figure 8:
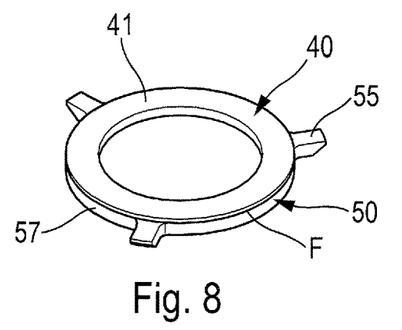
FIG. 8 shows a perspective view of the assembled filter unit of FIG. 5.

As shown in FIG. 7, the central opening of the lower filter support member 50 may advantageously have a central hexagonal support structure 51, with each apex of the hexagon 51 being connected to the peripheral inner edge 52 by a respective radial rib 53, thus defining seven apertures 54. Such a hexagonal central structure 51 provides maximum surface area while increasing structural support of the filter F during aerosol collection. Of course, this is just an example, and one could imagine any central support structure 51, whether polygonal or rounded, e.g. circular, and any number of radial ribs 53. The central support structure 51 and the radial ribs 53 may be of essentially triangular cross-sectional configuration such that at their upper extremity, they provide a narrow line of contact with the filter F, whilst for strength reasons the bottom portion of the ribs may be thicker.

The upper filter support member 40 comprises an upper ring 41 and a lower ring 42, which extends axially downwards from said upper ring 41, said upper and lower rings having the same internal diameter, and said upper ring 41 having an external diameter that is larger than the external diameter of said lower ring 42.

Figure 9:
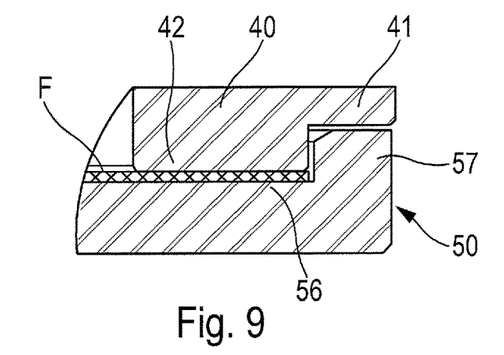
FIG. 9 is a sectional partial view through the assembled filter unit of FIG. 8.
Figure 10:
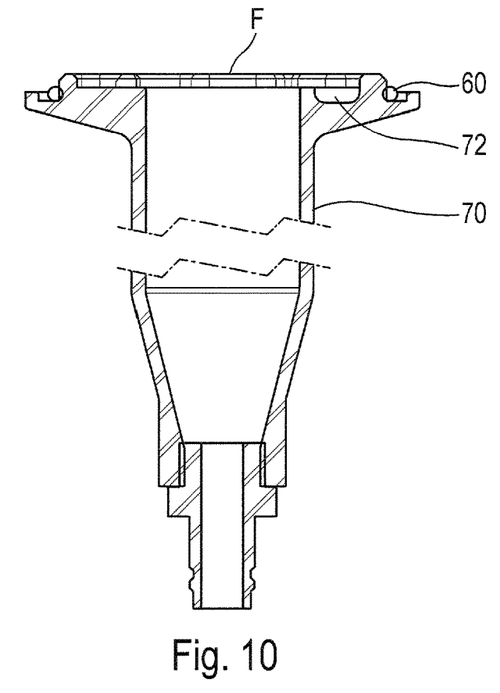
FIG. 10 is a sectional partial view through the lower body.
Figure 11:
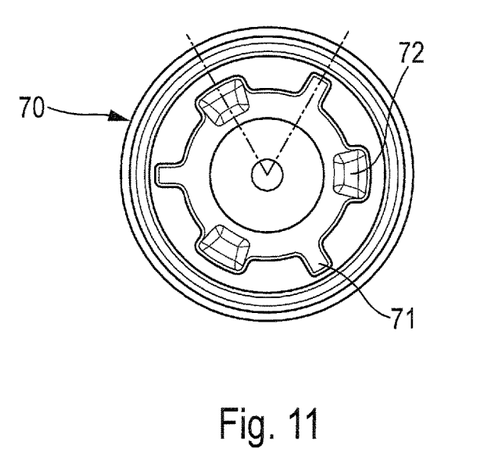
FIG. 11 is a top view of the top surface of said lower body.

The external rim of the filter F is thus retained between said inner flange 56 of the lower filter support member 50 and said lower ring 42 of the upper filter support member 40, as best seen on FIG. 9.

One function of the upper filter support member 40 is to provide a sealing element between the filter F and the lower filter support member 50 and to provide a suitable weight to prevent the filter F from lifting or separating from the lower filter support member 50 during dissolution studies.

The lower ring 42 of the upper filter support member 40 can be made in a range of heights to accommodate different filter thicknesses. Said height can also be modified to increase/decrease the compressive force upon clamping of the apparatus with the clamping device 80.

Suitable filters F for use in the apparatus of the invention are generally those having a nominal pore size in the range of 1 to 3 µm. Since, in the apparatus of the invention, the filter F is provided in-line in the flow pathway, is suitable filters F are preferably selected to have a pore size that is sufficiently small that the filter traps essentially all, and preferable not less than 90%, especially not less than 95% by weight of solids entrained in the air flow, whilst the resistance to air flow presented by the filter is relatively small.

Studies have shown that filters with a pore size of 3 µm is sufficiently fine for capturing aerosols. Whilst a pore size of at least 1 µm is preferred, in practice it is the air-permeability of the filter that influences its suitability in the apparatus of the invention, and filters with pore size of less than 1 µm may be used where they do not substantially increase the resistance to flow, for example, result in a flow rate reduction of not more than 15%, preferably not more than 10% relative to absence of a filter.

The lower body 70 receives the filter unit on its top surface. As seen on FIGS. 10 and 11, said top surface comprises the second O-ring 60, which provides the principle air path seal of the apparatus upon clamping. The top surface also comprises first recesses 71, adapted to cooperate with the radial projections 55 of the lower filter support member 50, to provide rotational alignment of the filter unit on the lower body 70. Second recesses 72 are provided to allow manual, semi-automatic or automatic extraction of the filter unit from the lower body 70 upon releasing the clamping device 80.

Figure 12:
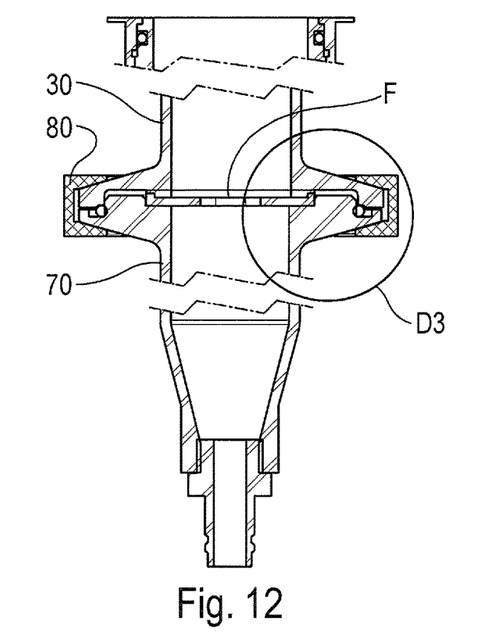
FIG. 12 is a sectional partial view through the upper body assembled on the lower body by the clamping device.
Figure 13:
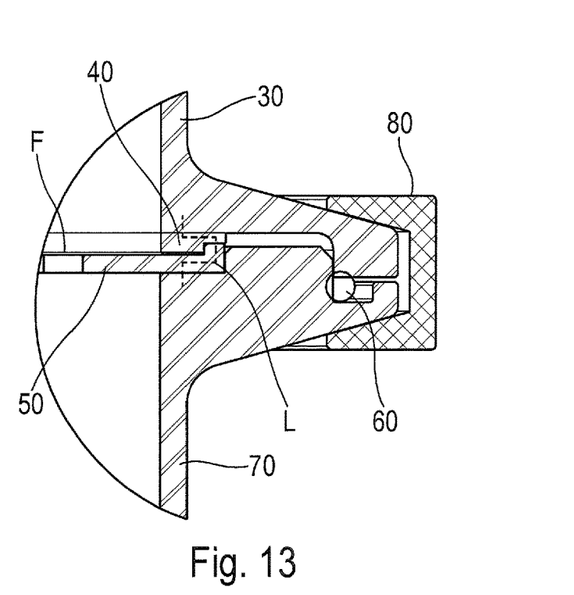
FIG. 13 is an enlarged view of detail D3 of FIG. 12.

FIGS. 12 and 13 show the upper and lower bodies 30, 70 assembled by the clamping device 80. The dashed line L in FIG. 13 shows the compressive force path. This ensures a controlled compression load on the filter F upon clamping. The force applied is balanced to ensure that filter structure is not damaged, whilst retaining and sealing the filter to the lower filter support member 50.

The clamping device 80 advantageously comprise two clamping halves rotatably connected to each other by a pin 81, and provided with a closure system. Said closure system can comprise a threaded shaft 82 cooperating with an appropriate nut 83. Other clamping devices, in particular other closure systems, could also be used.

The drug laden filter F, housed in the filter unit, can be removed from the lower body either manually, semi-automatically or automatically. This is facilitated by the second recesses 72 in the lower body 70.

Figure 19:
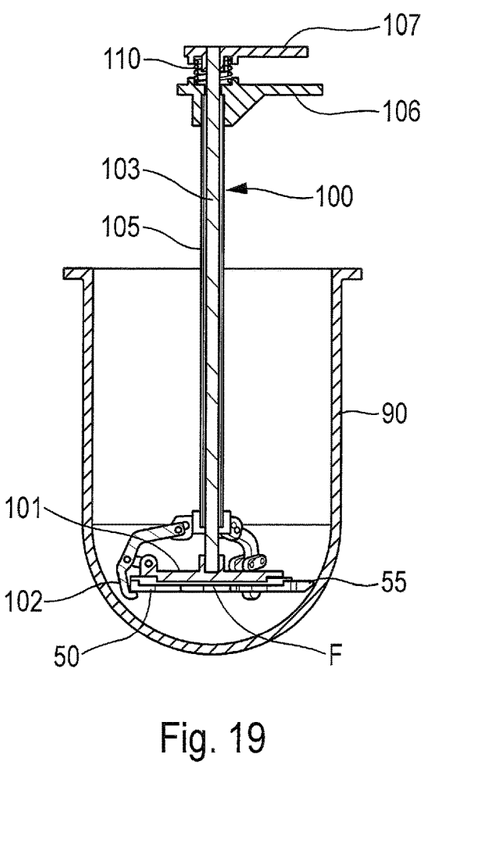
FIG. 19 shows the introduction of the filter unit of FIG. 5 in a dissolution vessel by using the quick-release system of FIG. 14.
Figure 20:
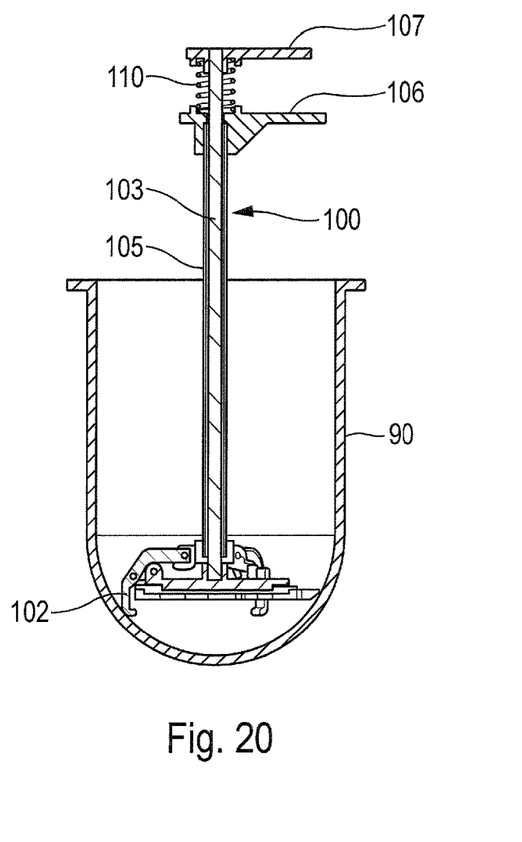
FIG. 20 is a similar view as FIG. 19, showing the release of the filter unit inside the dissolution vessel.

The loaded filter F can then be transferred to a secondary apparatus for testing. FIGS. 19 and 20 show the transfer to a dissolution vessel 90.

According to one aspect of the invention, the removal of the filter unit from lower body 70 can be made with a quick-release system 100, manually actuated, but which avoids any contact of humans with the filter unit.

Figure 14:
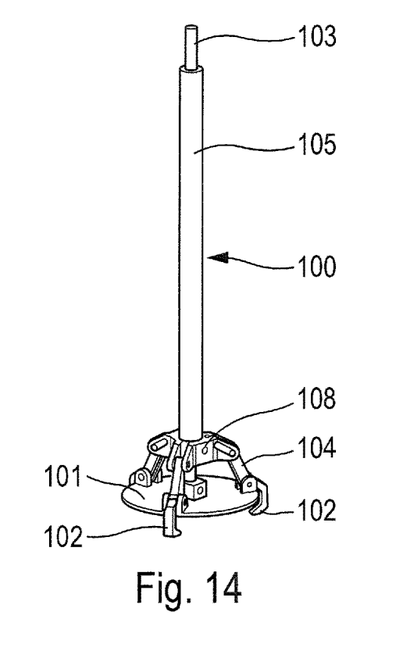
FIG. 14 is a perspective view of a quick-release system according to an advantageous embodiment of the present invention.
Figure 15:
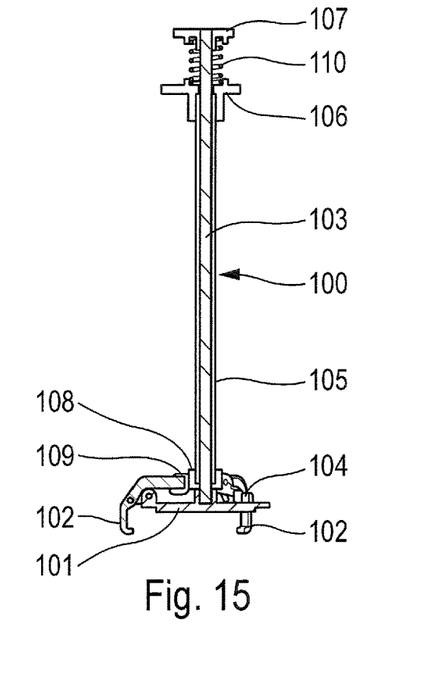
FIG. 15 is a sectional view through the quick-release system of FIG. 14.

An example of a quick-release system is shown on FIGS. 14 and 15.

Said quick-release system 100 comprises a clamp base 101, fixing means, preferably formed by retaining hooks 102, preferably three of them, an actuating rod 103, a link arm 104 and a main support 105. Actuation of the actuating rod 103 is triggered by a finger 106 and a thumb-actuator 107. The system further comprises a cam tree 108, a locking pin 109 and a spring 110.

Figure 16:
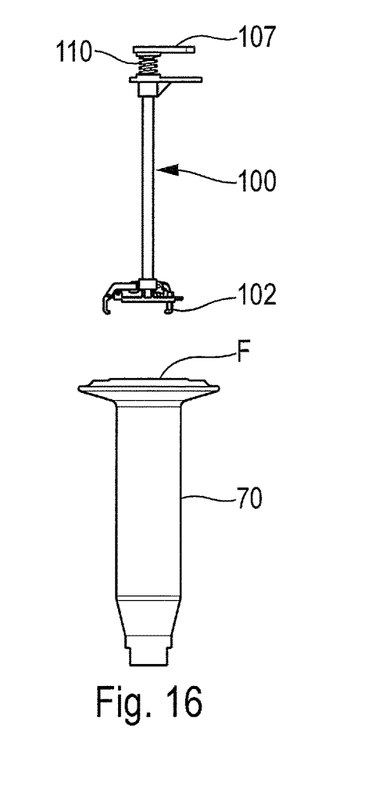
FIGS. 16 to 18 show three successive steps of the handling of the quick-release system of FIG. 14.
Figure 17:
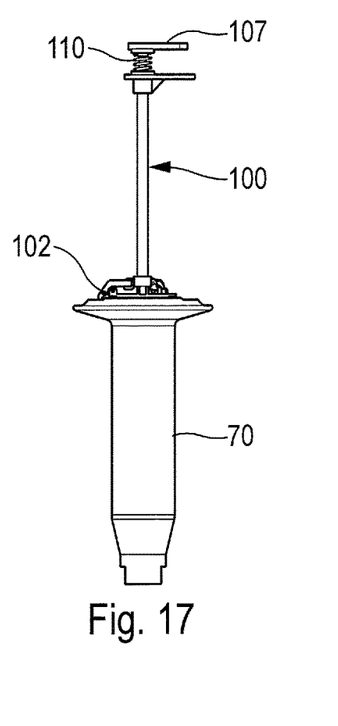
Figure 18:
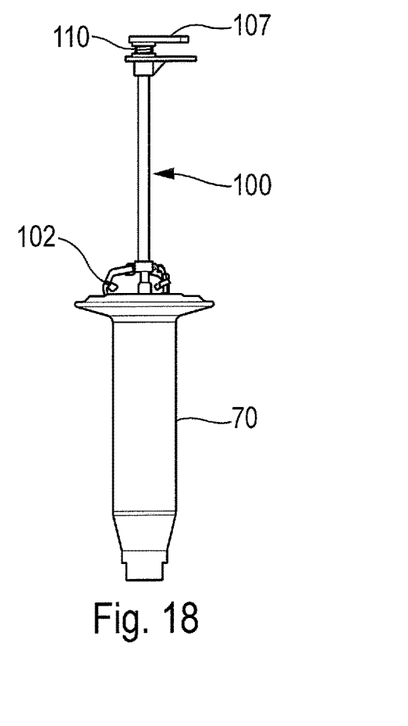

A series of figures that show how the system is used under operation is shown on FIGS. 16 to 18.

The quick-release system 100, with non-actuated thumb-actuator 107, and thus non-compressed spring 110 and open hooks 102, is moved towards the filter unit located on the top surface of the lower body 70. The open hooks 102 can enter the second recesses 72, and get positioned around the filter unit. Upon actuation of the thumb actuator 107, the actuating rod 103 moves downwards, thus compressing spring 110 and moving the hooks 102 radially inwards to a closing position in which they cooperate with the filter unit to retain the latter inside the closed hooks 102. The clamp base 101, formed substantially by a thin plate, comes over the filter F to protect it against the external environment.

The filter unit thus can safely be removed from the lower body, and transferred to the dissolution vessel, as shown in FIGS. 19 and 20. Upon release of the actuation force on the thumb-actuator 107, the compressed spring 110 can relax, and allow the rod 103 to return to its rest position, thus allowing the hooks 102 to open and release the filter unit inside the dissolution vessel 90.

Where in the foregoing description, integers or elements are mentioned which have known, obvious or foreseeable equivalents, then such equivalents are herein incorporated as if individually set forth. Reference should be made to the claims for determining the true scope of the present invention, which should be construed so as to encompass any such equivalents. It will also be appreciated by the reader that integers or features of the invention that are described as preferable, advantageous, convenient or the like are optional and do not limit the scope of the independent claims. Moreover, it is to be understood that such optional integers or features, whilst of possible benefit in some embodiments of the invention, may not be desirable, and may therefore be absent, in other embodiments.

The invention claimed is:

1. A system comprising:
an apparatus for collecting aerosolized respirable particles of an inhalable medicinal formulation, comprising an inlet for receiving an aerosolized dose of the medicinal formulation, a suction source for generating a pneumatic flow through the apparatus, a channel defining a pathway extending from said inlet to said suction source, and a dose collection section located in said pathway of said pneumatic flow through the apparatus, said dose collection section having an air-permeable filter, said filter extending across the pathway of said aerosolized respirable particles so as to retain particulate material therein on said filter, said dose collection section comprising:
an upper filter support member and a lower filter support member, said filter being circumferentially retained between said upper and lower support members to form a filter unit,
a lower body receiving said filter unit, said lower body having a top surface comprising recesses located around said filter unit,
a quick-release system comprising fixing means, such as hooks, movable between an open position and a closed position, wherein said fixing means, in said open position, can enter said recesses around said filter unit, and in said closed position, said fixing means can grab said filter unit, thus allowing removal of said filter unit from said lower body without any human contact on said filter unit.

2. A system according to claim 1, wherein said quick-release system further comprises a clamp base, an actuating rod having a thumb-actuator to trigger the actuation of said actuating rod, and a spring.

3. A system according to claim 1, wherein said lower filter support member comprises an outer ring connected to an inner flange projecting radially inwards from a lower surface of said outer ring, said inner flange having a peripheral inner edge defining a central opening, wherein said central opening has a central support structure connected to said peripheral inner edge by at least two radial ribs, thus defining multiple apertures.

4. A system according to claim 3, wherein said central support structure is hexagonal, with each apex of said hexagon being connected to the peripheral inner edge by a radial rib, thus defining seven apertures.

5. A system according to claim 3, wherein said upper filter support member comprises an upper ring and a lower ring, which extends axially downwards from said upper ring, said upper and lower rings having the same internal diameter, and said upper ring having an external diameter that is larger than the external diameter of said lower ring, wherein the external rim of said filter is retained between said inner flange of the lower filter support member and said lower ring of said upper filter support member.

6. A system according to claim 1, wherein said lower filter support member comprises at least one, preferably three, radial projections, extending radially outwards from the external periphery of said outer ring.

7. A system according to claim 6, wherein said top surface of said lower body comprises first recesses adapted to cooperate with said radial projections of the lower filter support member, to provide rotational alignment of the filter unit on said lower body.

8. A system according to claim 1, wherein the dose collection section comprises an inlet orifice, the filter being positioned opposed to said orifice, and the orifice being so dimensioned and configured that it has an unimpeded area that is no less than 75% of the area of the filter on which the dose will be collected;

wherein said suction source communicates with said pathway downstream of said filter unit;

wherein said filter unit has a filter support comprising one or more support members extending across the pathway on the surface of the filter opposed to the orifice for supporting a central region of the filter, the filter support defining two or more apertures and obstructing no more than 80% of the surface area of said opposed surface.

9. A system according to claim 8, wherein the orifice is so dimensioned and configured that it has an outlet area that is not less than 80%, preferably not less than 90%, of the area of said filter on which the dose will be collected.

10. A system according to claim 1, wherein said filter is selected from woven fabrics, nonwoven fabrics, meshes and air-permeable films.

11. A system according to claim 10, wherein the filter comprises a fabric formed from glass microfibers, synthetic cellulose based materials, or from filaments of a polymeric material selected from polycarbonate, polyester, polyolefins, polyamides, polyvinylchlorides and polyetheretherketones.

12. A system according to claim 10, wherein the filter comprises a metal mesh, for example a stainless steel mesh.

13. A system according to claim 1, wherein said filter has a pore size of not more than 5 μm, preferably not more than 3 μm.

14. A system according to claim 1, wherein said filter has a pore size of at least 1 μm.

15. A system according to claim 1, wherein said filter has an air permeability which is such that the filter generates a reduction in flow rate of not more than 20%, preferably not more than 15%, more preferably not more than 10% relative to absence of a filter.

* * * * *